United States Patent
Shinsky et al.

(10) Patent No.: US 10,179,000 B1
(45) Date of Patent: Jan. 15, 2019

(54) DEVICES FOR RETRIEVING AN OBSTRUCTION IN A BODILY DUCT OF A PATIENT

(71) Applicant: Highway 1 Medical, Inc., San Mateo, CA (US)

(72) Inventors: Vera Shinsky, Mountain View, CA (US); Scott D. Wilson, Woodside, CA (US)

(73) Assignee: Highway 1 Medical, Inc., San Mateo, CA (US)

( * ) Notice: Subject to any disclaimer, the term of this patent is extended or adjusted under 35 U.S.C. 154(b) by 0 days.

(21) Appl. No.: 15/887,173

(22) Filed: Feb. 2, 2018

(51) Int. Cl.
*A61B 17/221* (2006.01)

(52) U.S. Cl.
CPC .... *A61B 17/221* (2013.01); *A61B 2017/2215* (2013.01)

(58) Field of Classification Search
CPC ........... A61B 17/221; A61B 2017/2215; A61F 2/86–2/915
See application file for complete search history.

(56) References Cited

U.S. PATENT DOCUMENTS

| 5,102,417 | A | 4/1992 | Palmaz |
| 6,168,603 | B1 | 1/2001 | Leslie et al. |
| 6,402,771 | B1 | 6/2002 | Palmer et al. |
| 7,300,458 | B2 | 11/2007 | Henkes et al. |
| 8,088,140 | B2 | 1/2012 | Ferrera et al. |
| 8,945,143 | B2 | 2/2015 | Ferrera et al. |
| 9,072,537 | B2 | 7/2015 | Grandfield et al. |
| 2008/0051876 | A1* | 2/2008 | Ta .............................. A61F 2/91 623/1.16 |
| 2012/0209311 | A1* | 8/2012 | Grandfield ........... A61B 17/221 606/200 |
| 2015/0080937 | A1* | 3/2015 | Davidson ............. A61B 17/221 606/200 |
| 2015/0209165 | A1 | 7/2015 | Grandfield et al. |

* cited by examiner

*Primary Examiner* — Kathleen Holwerda
(74) *Attorney, Agent, or Firm* — Edell, Shapiro & Finnan, LLC

(57) ABSTRACT

A device for capturing and removing an obstruction in a bodily duct of a patient. The device includes a cylindrical body having a circumference and a longitudinal axis. According to some implementations the cylindrical body is comprised of a plurality of closed cell structures arranged in diagonal rows around the longitudinal axis. At least some of closed cell structures have substantially the same shape and size. According to some implementations at least some of the closed cell structures of substantially the same shape and size occupy a same circumferential location in the cylindrical body and are longitudinally separated from one another by no less than two, three, four or more diagonal rows of closed cell structures. According to other implementations the closed cell structures include diagonally extending struts having at least a curve portion and a straight portion.

17 Claims, 9 Drawing Sheets

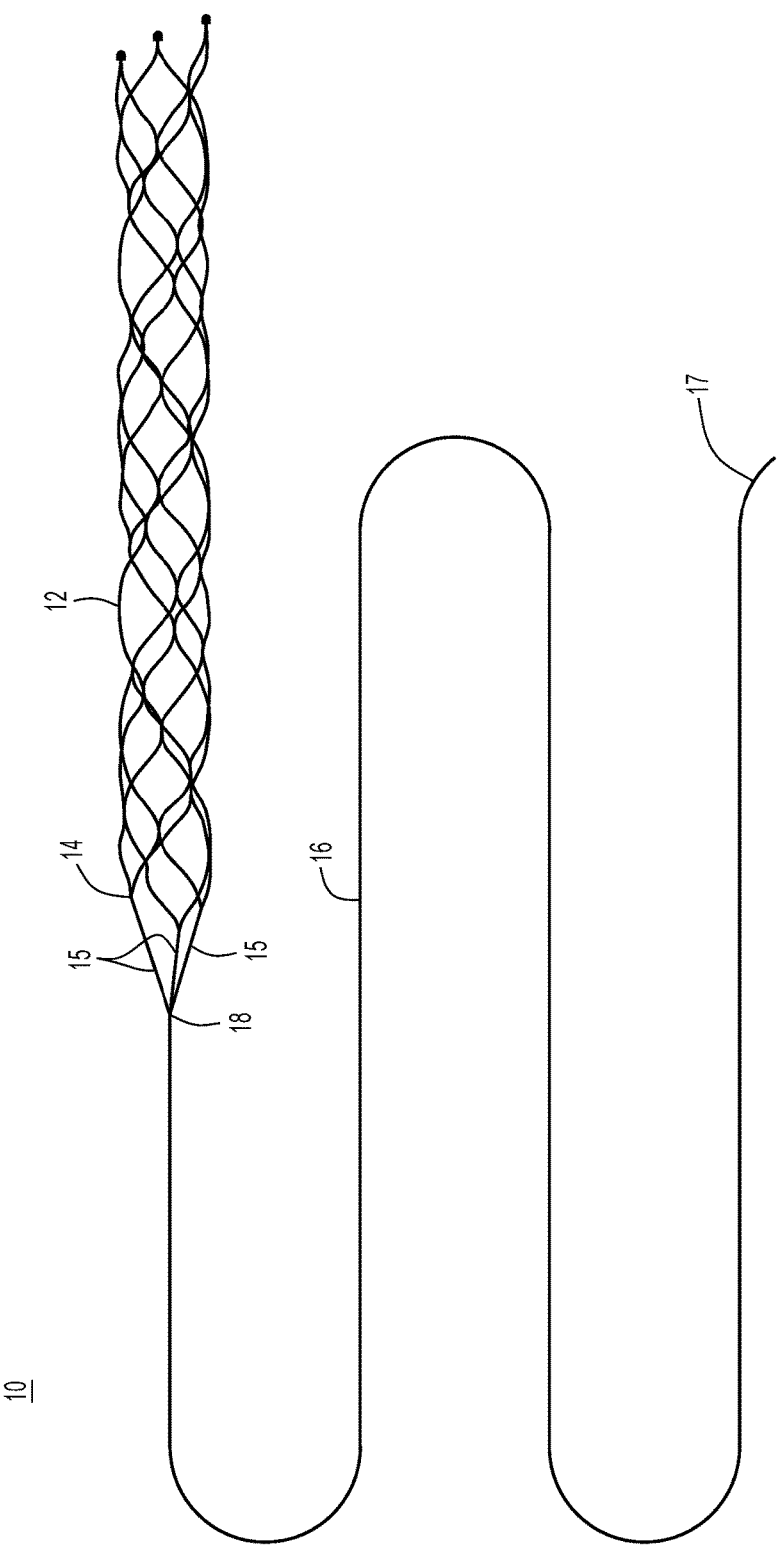

US 10,179,000 B1

DEVICES FOR RETRIEVING AN OBSTRUCTION IN A BODILY DUCT OF A PATIENT

TECHNICAL FIELD

The present disclosure relates to devices for retrieving obstructions from bodily ducts.

BACKGROUND

An obstruction in a bodily duct of a patient can lead to chronic health issues, and even death, if the obstruction is left in place.

An example of such an obstruction is an embolus located in a blood vessel of a patient. The embolus may be a blood clot (thrombus), a fat globule (fat embolism) or foreign material. An embolism can cause partial or total blockage of blood flow in the affected vessel, such as a vessel in the neurovasculature of a patient. The capture and removal of such blockages can prevent the occurrence of a stroke or at least partially reverse the effects of a stroke.

A urinary tract obstruction is another example in which a blockage inhibits the flow of urine through its normal path (the urinary tract), including the kidneys, ureters, bladder, and urethra. Blockage can be complete or partial and can lead to kidney damage, kidney stones, and infection if not removed.

SUMMARY OF THE DISCLOSURE

Disclosed herein are devices for capturing and removing obstructions from bodily ducts of a patient.

According to some implementations a device for retrieving an obstruction in a bodily duct of a patient is provided that comprises a cylindrical body having a circumference and a longitudinal axis and including a plurality of cell structures of substantially the same size and shape arranged in diagonal rows around the longitudinal axis. According to some implementations the plurality of cell structures each includes first, second, third, fourth, fifth and sixth struts, each of the first, second, third, fourth, fifth and sixth struts having a proximal end and a distal end. According to some implementations the proximal end of the first strut is coupled to the proximal end of the second strut, the distal end of the third strut is coupled to the distal end of the fourth strut, the distal end of the first strut is coupled to the proximal end of the fifth strut, the proximal end of the third strut is coupled to the distal end of the fifth strut, the distal end of the second strut is coupled to the proximal end of the sixth strut, the proximal end of the fourth strut is coupled to the distal end of the sixth strut. According to some implementations the proximal and distal ends of the fifth strut are longitudinally aligned with one another and reside at a first circumferential location and the proximal and distal ends of the sixth strut are longitudinally aligned with one another and reside at a second circumferential location, the second circumferential location being spaced apart from the first circumferential location. According to some implementations, when the retrieval device is cut longitudinally and laid flat on a surface at least a first portion of each of the first, second, third and fourth struts is curved and at least a second portion of each of the first, second, third and fourth struts is straight.

According to other implementations, each of the first, second, third and fourth struts has a proximal end portion, a distal end portion and a mid-portion with the mid-portion being located between the proximal and distal end portions, the first and second end portions being curved and the mid-portion being straight when the device is cut longitudinally and laid flat on a surface.

According to other implementations a device for capturing and removing an obstruction in a bodily duct of a patient is provided that comprises a cylindrical body having a circumference and a longitudinal axis and including a plurality of closed cell structures arranged in a plurality of diagonal rows disposed around the longitudinal axis. At least some of the plurality of closed cell structures being substantially the same shape and size, at least some of the closed cells structures of substantially the same shape and size occupying a same circumferential location in the cylindrical body and being longitudinally separated from one another by no less than two, three, four or more diagonal rows of closed cell structures.

These and other advantages and features will become evident in view of the drawings and the detailed description.

BRIEF DESCRIPTION OF THE DRAWINGS

FIG. 1 shows a perspective view of an obstruction retrieval system according to some implementations;

DETAILED DESCRIPTION

Figure 2A:
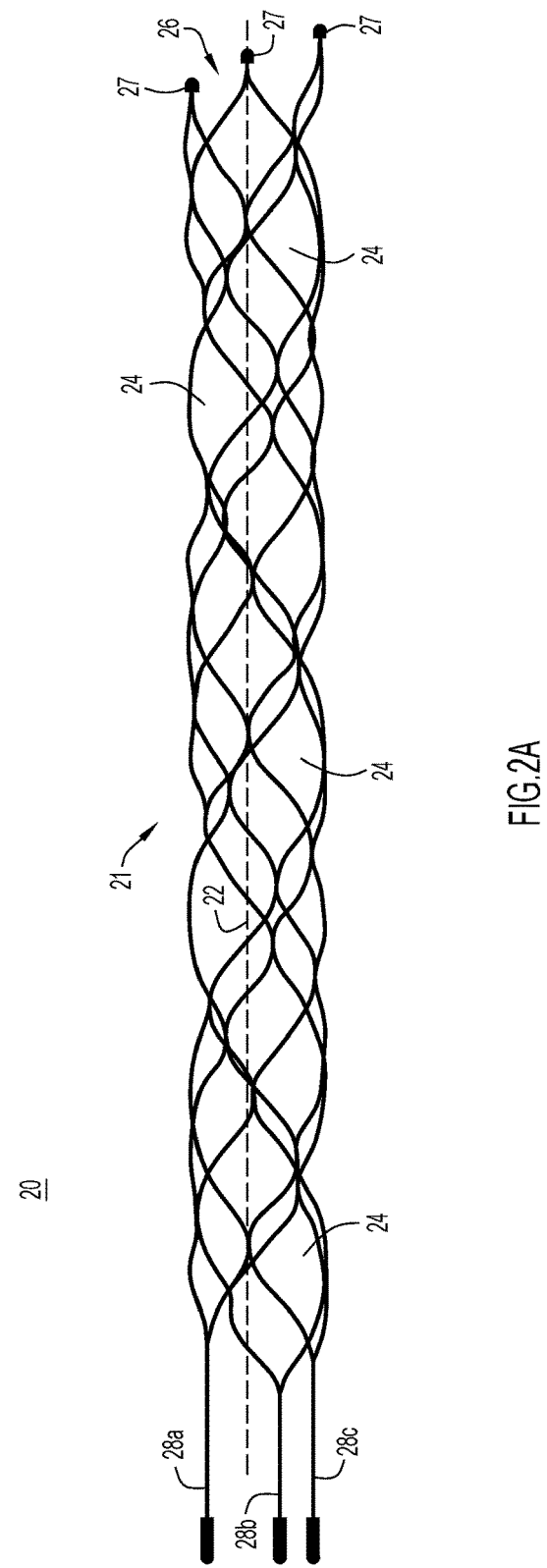
FIG. 2A is a perspective view of an obstruction retrieval device according to some implementations.

FIG. 1 shows a perspective view of an obstruction retrieval system 10 according to one implementation. The retrieval system includes a self-expanding retrieval device 12 comprising a cylindrical body, such as those depicted in FIGS. 2A and 3A, having a proximal end 14 that is coupled to the distal end 18 of an elongate wire 16 via a plurality of antennas 15. Each of the plurality of antennas 15 is connected at a proximal end to the distal end 18 of the elongate wire 16, and connected at a distal end to the proximal end 14 of the cylindrical body. As discussed below in more detail, according to some implementations the proximal end of the cylindrical body is coupled to the distal end of the elongate wire by a single antenna that extends proximally from a side of the cylindrical body.

In the example of retrieving an embolus from a blood vessel in the neurovasculature of a patient, according to some implementations, in use the self-expanding retrieval device is loaded into a distal end portion of a delivery catheter (not shown) and delivered with the delivery catheter to the site of the embolus. According to some implementations the distal end portion of the delivery catheter is positioned across the embolus and then withdrawn proximally to deploy the retrieval device into the embolus. According to other implementations the distal end portion of the delivery catheter that carries the retrieval device is positioned distal to the embolus and then proximally withdrawn to deploy the retrieval device at a location distal to the embolus. In such a case the embolus is captured by retracting the retrieval device 12 proximally into the embolus. This is accomplished by a clinician pulling on a proximal end portion 17 of the elongate wire 14 that resides outside the patient.

Keeping with the neurovascular obstruction example, upon the embolus being at least partially captured inside the retrieval device 12, the retrieval device and the delivery catheter are singularly or together proximally withdrawn to effectuate a removal of the obstruction from the patient. According to some implementations the retrieval device 12 is at least partially withdrawn into the lumen of the delivery catheter during the removal process.

According to some implementations the retrieval device 12 has a length of between about 10 millimeters to about 100 millimeters and the elongate wire 14 has a length of between about 150 centimeters to about 250 centimeters.

As will be discussed in more detail below, the anatomy of certain bodily ducts is tortuous having regions of tight bends. A problem with many existing retrieval devices is that the captured obstruction tends to disengage with the retrieval device as the retrieval device is maneuvered through this tortuous path. The retrieval devices disclosed herein comprise features that enhance their ability to capture an obstruction and to more effectively remove the obstruction from the patient through a tortuous path comprising tight bends.

Figure 2B:
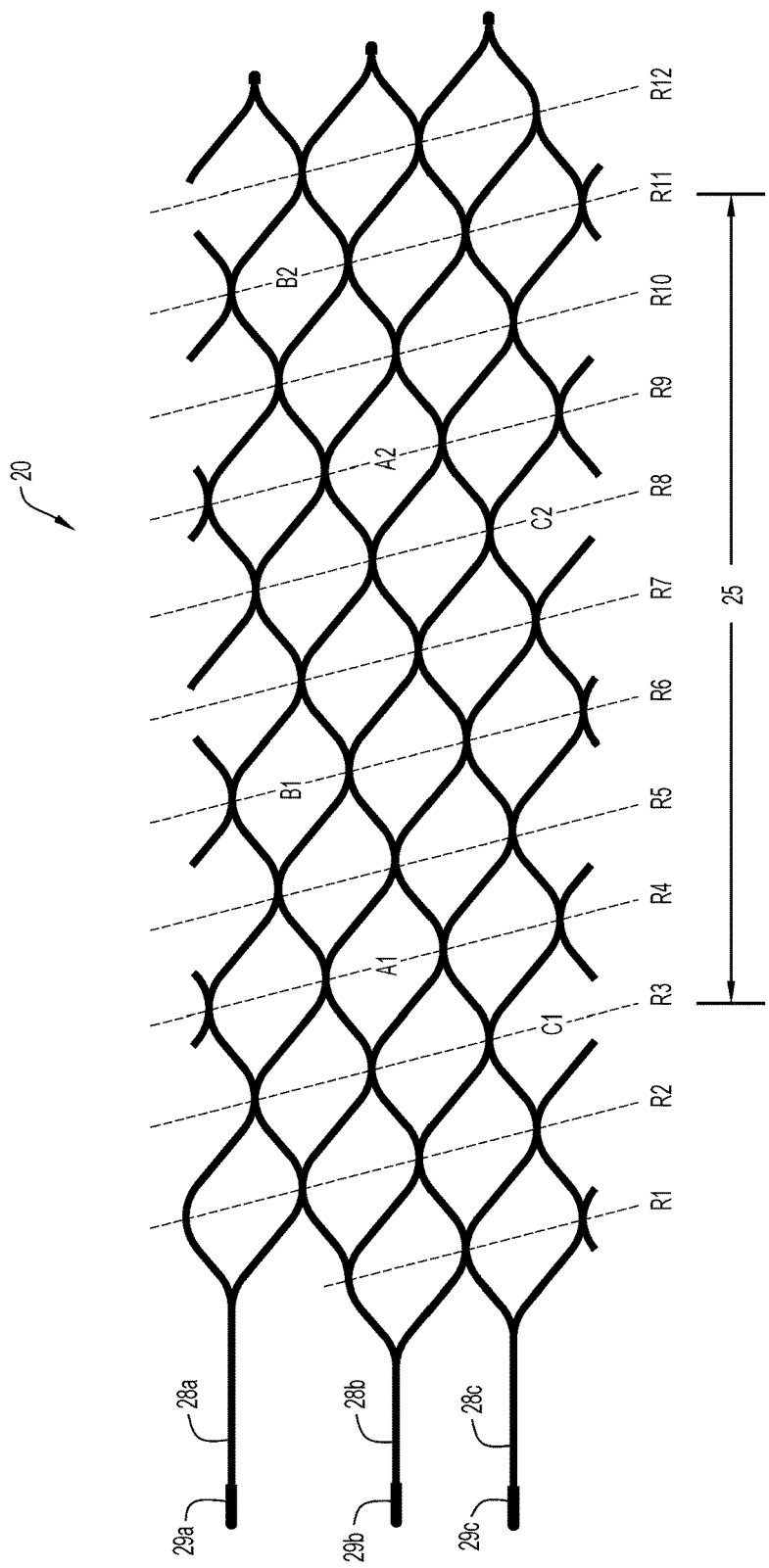
FIG. 2B is a view of the obstruction retrieval device of FIG. 2A as if the device were cut along a line parallel to its longitudinal axis and laid flat on a surface.
Figure 3A:
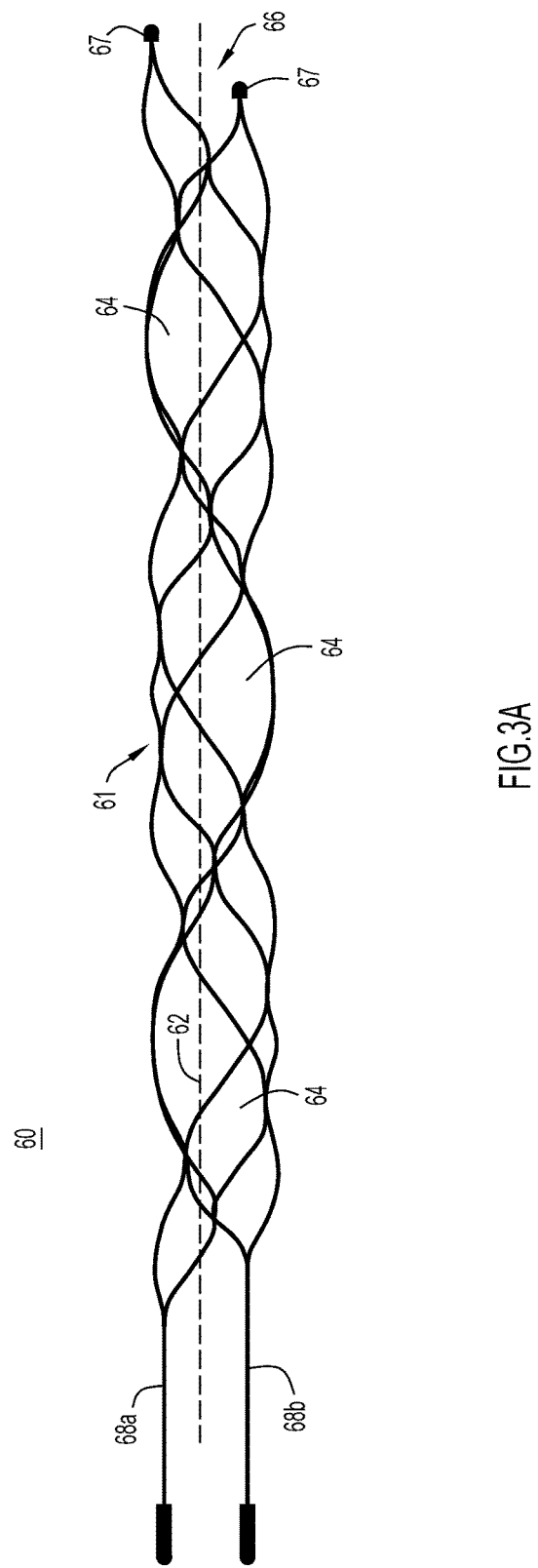
FIG. 3A is a perspective view of an obstruction retrieval device according to another implementation.
Figure 3B:
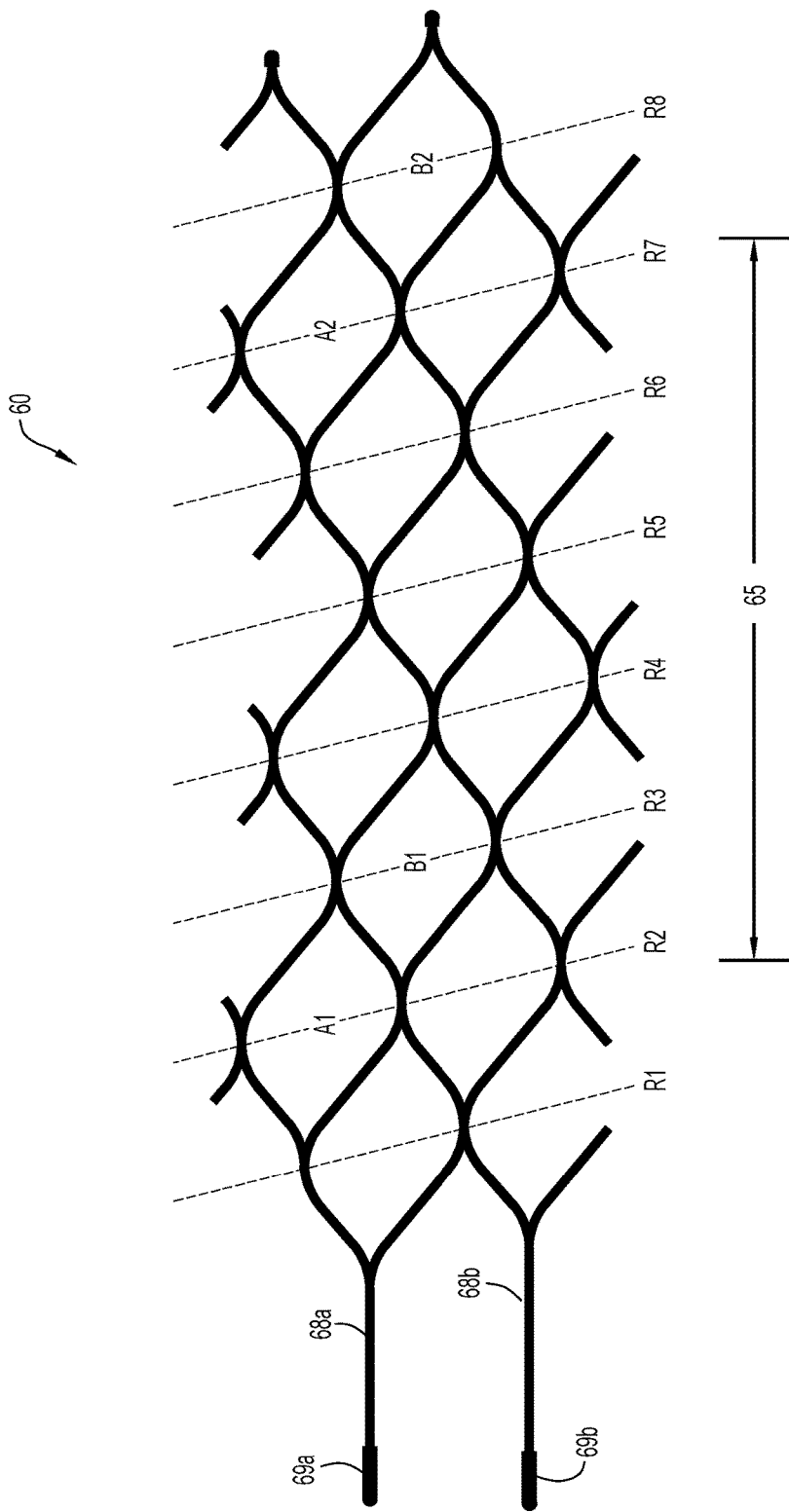
FIG. 3B is a view of the obstruction retrieval device of FIG. 3A as if the device were cut along a line parallel to its longitudinal axis and laid flat on a surface.

FIGS. 2A and 3A illustrate exemplary retrieval devices 20 and 60, respectively. FIGS. 2B and 3B respectively show the retrieval devices 20 and 60 as if the retrieval devices were cut along a line parallel to their longitudinal axis and laid flat on a surface. Each of the retrieval devices 20 and 60 respectively comprises a cylindrical body 21 and 61 having a central longitudinal axis 22 and 62. Each of the cylindrical bodies 20 and 60 is respectively comprised of a plurality of closed cell structures 24 and 64 that are disposed about its longitudinal axis. FIGS. 2A and 3A represent the retrieval devices in an as-cut configuration typically resulting from the laser cutting of a metallic cylindrical tube made of, for example, a nickel-titanium alloy. It is important to note, however, that other manufacturing methods may be used to construct the retrieval devices disclosed herein.

In the example of FIGS. 2A and 2B, the retrieval device 20 includes twelve diagonal rows of cell structures R1-R12 and possesses a central body portion 25 that extends between rows R3 and R11. According to some implementation, the cell structures that form the central body portion 25 are of substantially the same size and shape. According to some implementations, each row of cell structures in the central body portion 25 includes four cell structures that together surround the longitudinal axis 22 of the cylindrical body 21.

In the example of FIGS. 3A and 3B, the retrieval device 60 includes eight diagonal rows of cell structures R1-R8 and possesses a central body portion 65 that extends between rows R2 and R7. According to some implementation, the cell structures that form the central body portion 65 are of substantially the same size and shape. According to some implementations, each row of cell structures in the central body portion 65 includes three cell structures that together surround the longitudinal axis 62 of the cylindrical body 61.

Retrieval devices having less than eight rows of cell structures, more than twelve rows of cell structures, and greater than four cell structures in a given row are also contemplated.

As explained above in the discussion of FIG. 1, the cylindrical body portion of the retrieval device 12 is coupled to the distal end of an elongate wire 16 via the use of one or more antennas 15 that extend proximally from the proximal end 14 of the cylindrical body.

In the implementation of FIGS. 2A and 2B the retrieval device 20 includes three antennas 28a, 28b and 28c that are straight and arranged parallel to the longitudinal axis 22 of the cylindrical body 21 in the as-cut configuration as shown in FIG. 2A. After the retriever 20 has been formed and polished, tabs or loops 29a-c that may be located at the proximal-most end of the antennas 28a-c are removed. The antennas 28a-c are then connected to the distal end of an elongate member 16 like that disclosed above in conjunction with the description of FIG. 1. That is, the proximal ends of the antennas 28a-c converge to a common area where they are attached to the distal end 18 of the elongate wire 16. By virtue of their convergence, the antennas 28a-c cause the retrieval device 20 to have a partially closed proximal end. According to other implementations the retrieval device 20 comprises a single antenna. For example, according some implementations the retrieval device 20 includes a single antenna that extends from a side of the cylindrical body 61 so that the proximal end of the retrieval device is fully open.

In the implementation of FIGS. 3A and 3B the retrieval device 60 includes two antennas 68a and 68b that are straight and arranged parallel to the longitudinal axis 62 of the cylindrical body 61 in the as-cut configuration. After the retriever 60 has been cut and polished, the proximal ends of the antennas 68a-b, which may comprise tabs 69a-b, are connected to the distal end of an elongate member 16 like that disclosed above in conjunction with the description of FIG. 1. That is, the proximal ends of the antennas 68a-b converge to a common area where they are attached to the distal end 18 of the elongate wire 16. By virtue of their convergence, the antennas 28a-b cause the retrieval device 20 to have a partially closed proximal end. According to other implementations the retrieval device 60 comprises fewer or more than three antennas. For example, according some implementations the retrieval device 60 includes a single antenna that extends from a side of the cylindrical body so that the proximal end of the retrieval device is fully open.

In the implementations of FIGS. 2A and 3A, the distal end of the retrieval devices 20 and 60 each respectively comprises an open distal end 26 and 66. According to other implementations the distal ends of the retrieval devices may be partially closed, for example, by joining together the distal-most end segments 27 and 67 of the devices. In the example of FIGS. 2A and 3A, according to some implementations the distal-most end segments 27 and 67 comprise features on which radiopaque markers may be affixed.

According to some implementations, the cylindrical body 21 of retrieval device 20 has a length of about 30 millimeters and an expanded outer diameter of about 5 millimeters. According to some implementations, the cylindrical body of retrieval device 60 has a length of about 20 millimeters and an expanded outer diameter of about 3 millimeters.

In terms of capturing an obstruction (e.g. an embolus) in a stent-like retrieval device like those disclosed herein, the effectiveness of capturing the obstruction is compromised in the current state of the art retrieval devices as a result of the frequency by which the longitudinal and circumferential location of like (e.g. same size and shape) cell structures are repeated. To address this problem, according to some implementations, like cell structures in retrieval devices 20 and 60 occupying a same circumferential location are separated by no less than two diagonal rows. In the implementations depicted in FIGS. 2B and 3B, like cell structures occupying a same circumferential location are separated by no less than four diagonal rows. An advantage of these configurations is that a greater degree of irregularity exits in the structure of the retrieval device along its length that enhances its ability to entrap an obstruction. This is a result of the obstruction being exposed to a greater number of different geometries along the length of the retrieval device which reduces slippage and improves integration of the obstruction into the retrieval device.

With reference to FIG. 2B, like cell structures A1 and A2 occupy a same circumferential location in the central body portion 25 of the cylindrical body 21 with cell structure A1 residing in diagonal row R4 and cell structure A2 residing in diagonal row R9 with there being four intervening rows R5-R8 separating cell structures A1 and A2. Likewise, like cell structures B1 and B2 occupy a same circumferential location in the central body portion 25 of the cylindrical body 21 with cell structure B1 residing in diagonal row R6 and cell structure B2 residing in diagonal row R11 with there being four intervening rows R7-R10 separating cell structures B1 and B2. In addition, like cell structures C1 and C2 occupy a same circumferential location in the central body portion 25 of the cylindrical body 21 with cell structure C1 residing in diagonal row R3 and cell structure C2 residing in diagonal row R8 with there being four intervening rows R4-R7 separating cell structures C1 and C2. According to other implementations, like cell structures occupying a same circumferential location are separated by no less than three intervening diagonal rows of cell structures.

With reference to FIG. 3B, like cell structures A1 and A2 occupy a same circumferential location in the central body portion 65 of the cylindrical body 61 with cell structure A1 residing in diagonal row R2 and cell structure A2 residing in diagonal row R7 with there being four intervening rows R3-R6 separating cell structures A1 and A2. Likewise, like cell structures B1 and B2 occupy a same circumferential location in the central body portion 65 of the cylindrical body 61 with cell structure B1 residing in diagonal row R3 and cell structure B2 residing in diagonal row R8 with there being four intervening rows R4-R7 separating cell structures B1 and B2. According to other implementations, like cell structures occupying a same circumferential location are separated by no less than three intervening diagonal rows of cell structures.

Figure 2C:
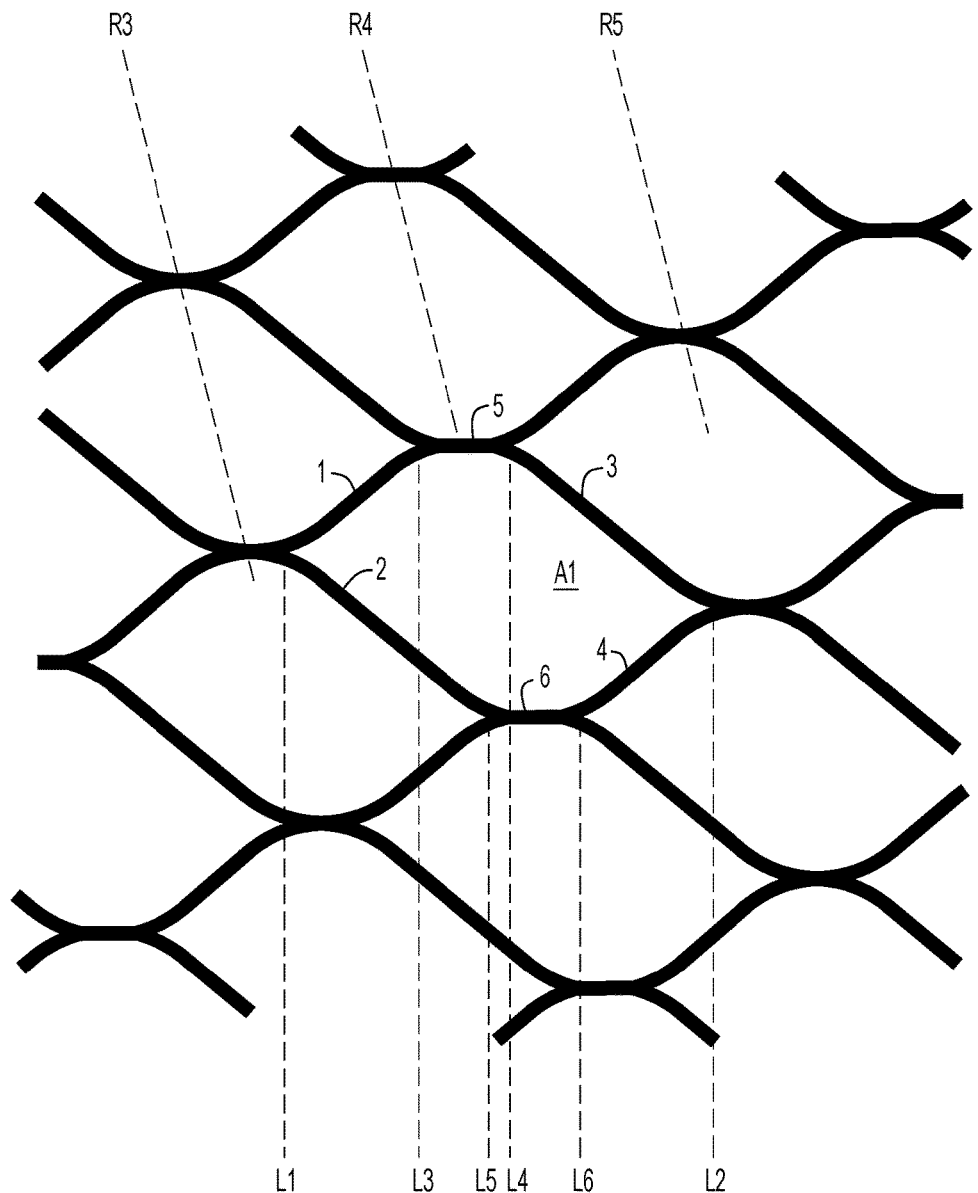
FIGS. 2C and 2D each are an enlarged view of a portion of the cell structures depicted in FIG. 2B.

FIG. 2C is an enlarged view of rows R3-R5 located in the central body portion 25 of retrieval device 20 with cell structure A1 residing in row R4. The configuration of cell structure A1 is representative of at least a majority of the cell structures within the retrieval device 20. Cell structure A1 includes a first strut 1, a second strut 2, a third strut 3, a fourth strut 4, a fifth strut 5 and a sixth strut 6, with each of the first, second, third, fourth, fifth and sixth struts having a proximal end and a distal end. The proximal end of the first strut 1 is coupled to the proximal end of the second strut 2 at a first longitudinal location L1, the distal end of the third strut 3 is coupled to the distal end of the fourth strut 4 at a second longitudinal location L2 distal to the first longitudinal location L1, the distal end of the first strut 1 is coupled to the proximal end of the fifth strut 5 at a third longitudinal location L3 that is located between the first and second longitudinal locations L1 and L2, the proximal end of the third strut 3 is coupled to the distal end of the fifth strut 5 at a fourth longitudinal location L4 located between the second and third longitudinal locations L2 and L3, the distal end of the second strut 2 is coupled to the proximal end of the sixth strut 6 at a fifth longitudinal location L5 that is located between the second and third longitudinal locations L2 and L3, the proximal end of the fourth strut 4 is coupled to the distal end of the sixth strut 6 at a sixth longitudinal location L6 that is located between the second and fifth longitudinal locations L2 and L5.

As best seen in FIGS. 2B and 3B, among the plurality of cell structures in retrieval devices 20 and 60, adjacent cell structures share at least one of the first, second, third, fourth, fifth and sixth struts with one another with the adjacent cell structures being both longitudinally and circumferentially offset from one another.

In the implementation of FIG. 2C, when the cylindrical body 21 of the retrieval device 20 is cut longitudinally and laid flat on a surface the third and fourth longitudinal locations L3 and L4 are longitudinally aligned with one another (that is, a straight line drawn between longitudinal locations L3 and L4 is parallel to the longitudinal axis 22 of the cylindrical body 21) and reside at a common first circumferential location, and the fifth and sixth longitudinal locations L5 and L6 are longitudinally aligned with one another (that is, a straight line drawn between longitudinal locations L5 and L6 is parallel to the longitudinal axis 22 of the cylindrical body 21) and reside at a common second circumferential location with the second circumferential location being spaced apart from the first circumferential location.

According to some implementations, when the cylindrical body 21 of the retrieval device 20 is cut longitudinally and laid flat on a surface at least one of the fifth strut 5 and sixth strut 6 is straight. According to other implementations each of the fifth strut 5 and sixth strut 6 is straight as shown in FIG. 2C. An advantage of one or both of the fifth and sixth struts being straight is that it advantageously endows the retriever 20 with a greater stiffness along its length than would otherwise exist if the struts were curved.

According to some implementations the fourth longitudinal location L4 and fifth longitudinal location L5 are circumferentially non-aligned with one another as shown in FIG. 2C. According to other implementations the fourth longitudinal location L4 and fifth longitudinal location L5 are circumferentially aligned with one another. A circumferentially alignment of the fourth and fifth longitudinal locations circumferentially aligns the distal end of the fifth strut 5 with the proximal end of the sixth strut 6 to produce a longitudinally continuous straight section within the cell structure A1, albeit circumferentially offset, that assists in providing the retriever with zones of enhanced stiffness.

As discussed above, a problem associated with removing a captured obstruction from a patient through a tortuous pathway is that when the retrieval device carrying the obstruction encounters and conforms to a tight bend, the obstruction is prone to being at least partially dislodged from the retriever. An advantage of providing a retriever with enhanced longitudinal stiffness is that it allows the retriever to at least partially straighten the bends through which it passes during the obstruction removal process. This reduces the risk of the obstruction being dislodge from the retrieval device as it is carried across the bends.

Another advantage of providing zones of enhanced longitudinal stiffness within the retrieval device is that it reduces the risk of the retrieval device buckling in procedures requiring the retrieval device to be pushed through the delivery catheter and/or through the bodily duct of the patient.

Figure 2D:
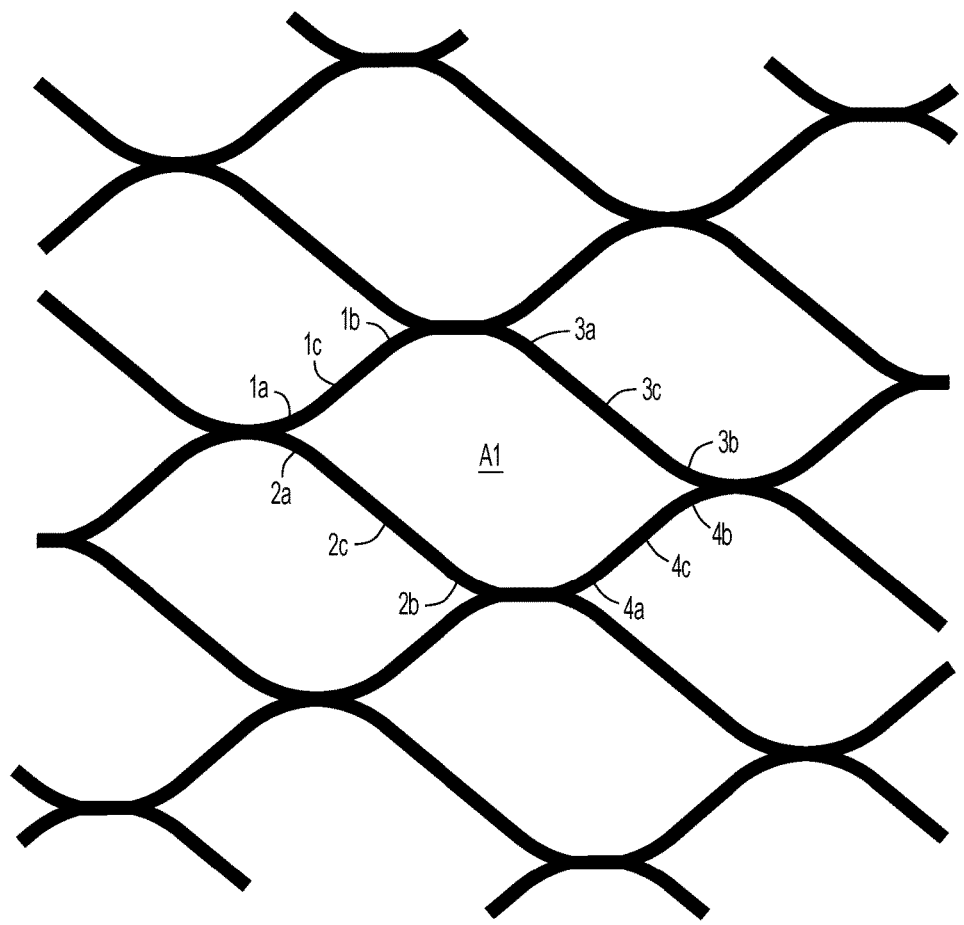

According to some implementations when the device is cut longitudinally and laid flat on a surface, as depicted in FIG. 2D, one or more or all of the first strut 1, second strut 2, third strut 3 and fourth strut 4 has a curved proximal end portion, a curved distal end portion and a straight portion located between the curved proximal and distal end portions. According to some implementations the straight portion is located in a middle portion of the strut. The curved proximal and distal end portions 1a, 1b, 2a, 2b, 3a, 3b, 4a, 4b of struts 1-4 contribute to providing a smooth transition between the connected struts of the cell structure and also provide the retrieval device 20 with a requisite amount of flexibility to enable it to navigate through the anatomy of a patient. The straight portion 1c, 2c, 3c, 4c of struts 1-4 enhances the longitudinal stiffness of the retrieval device 20 to provide the retrieval device with an ability to at least partially straighten the bends through which it passes during an obstruction removal process. As explained above, this reduces the risk of the obstruction being dislodged from the retrieval device as it is carried across tight bends. Another advantage of the mid-portion being straight is that it reduces the risk of the retrieval device buckling (as compared to entirely curved struts) in procedures requiring the retrieval device to be pushed through the delivery catheter and/or through the bodily duct of the patient.

According to some implementations one or more or all of struts 1-4 includes one or more straight portion that cumulatively occupy 20% to 80% of the overall length of the respective strut. According to other implementations one or more or all of struts 1-4 includes one or more straight portions that cumulatively occupy 30% to 70% of the overall length of the respective strut. According to some implementations one or more or all of struts 1-4 includes a single continuous straight portion that occupies 20% to 80% of the overall length of the respective strut. According to other implementations one or more or all of struts 1-4 includes a single continuous straight portion that occupies 30% to 70% of the overall length of the respective strut.

Figure 2E:
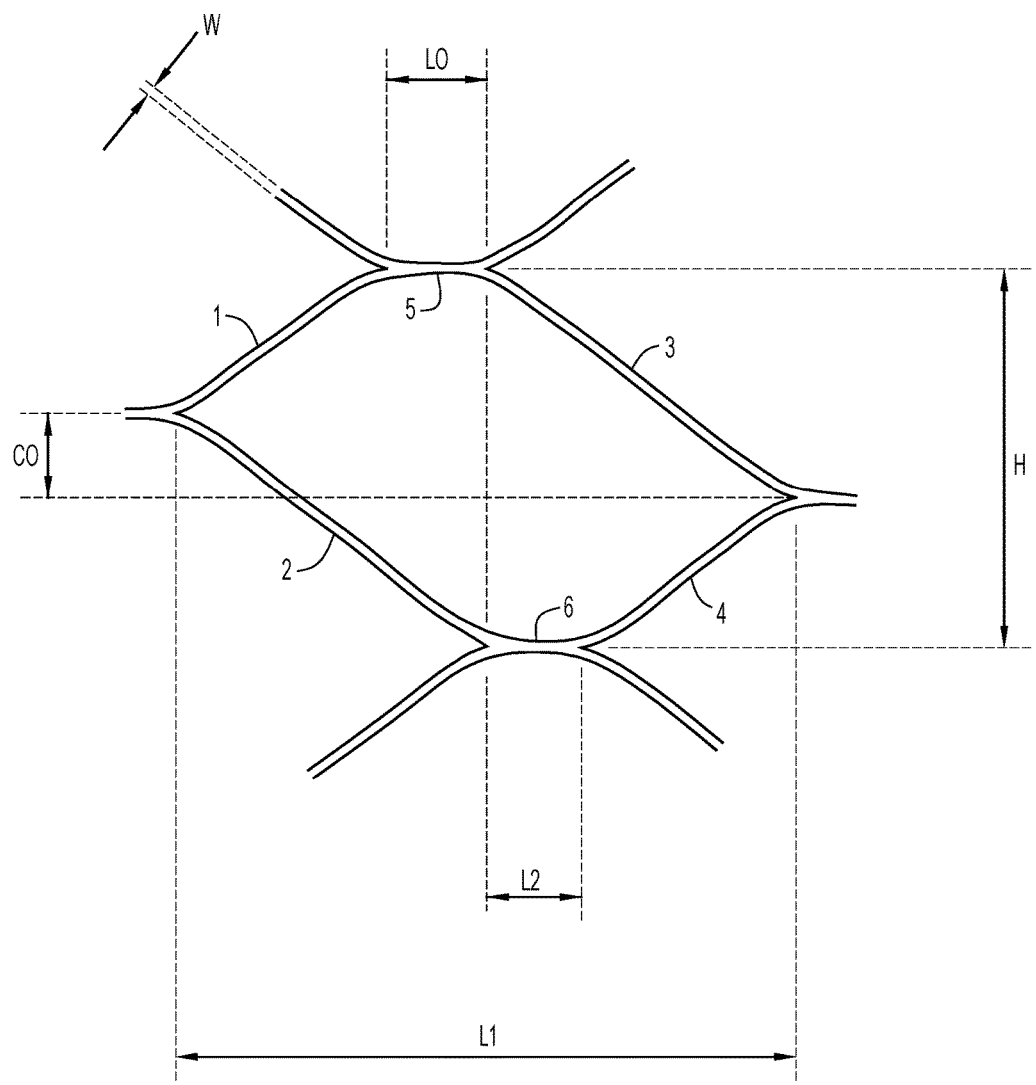
FIG. 2E illustrates dimensional characteristics of cell structures of an obstruction retrieval device according to some implementations.

As noted above, according to some implementations the cylindrical body 21 of retrieval device 20 has a length of about 30 millimeters and an expanded outer diameter of about 5 millimeters. With reference to FIG. 2E, according to some implementations the cell structures in the central body portion 25 of retrieval device 20 have a cell height H of between about 4.3 millimeters and about 4.6 millimeters, a cell length L1 of between about 4.6 millimeters and about 4.8 millimeters, a circumferential offset CO of between about 0.7 millimeters and about 0.8 millimeters, a longitudinal offset LO of between about 0.7 millimeters and about 0.9 millimeters, a strut width W of between about 0.07 millimeters and about 0.08 millimeters, with struts 5 and 6 having a length L2 of between about 0.9 millimeters to about 1.0 millimeters.

According to some implementations the cylindrical body 61 of retrieval device 60 has a length of about 20 millimeters and an expanded outer diameter of about 3 millimeters. With reference to FIG. 2E, according to some implementations the cell structures in the central body portion 65 of retrieval device 60 have a cell height H of between about 3.7 millimeters and about 3.95 millimeters, a cell length L1 of between about 4.9 millimeters and about 5.5 millimeters, a circumferential offset CO of between about 0.7 millimeters and about 0.8 millimeters, a longitudinal offset LO of between about 1.15 millimeters and about 1.25 millimeters, a strut width W of between about 0.07 millimeters and about 0.08 millimeters, with struts 5 and 6 having a length L2 of between about 0.9 millimeters to about 1.0 millimeters.

As discussed above, retrieval devices 20 and 60 may be coupled to the distal end of an elongate wire 16 by one or more antennas that extend proximally from a proximal end of the cylindrical bodies 21 and 61, respectively. According to some implementations in the as-cut configuration of the retrieval devices 20 and 60, the one or more antennas are straight and aligned parallel to the longitudinal axis of the cylindrical body as shown in FIGS. 2A, 2B, 3A and 3B with at least one of the antennas being longitudinally aligned with the proximal and distal ends of at least one of the fifth struts 5 and/or with the proximal and distal ends of at least one of the sixth struts 6. That is, a line extending between the straight antenna and across the proximal and distal ends of at least one of the fifth and sixth struts is straight and disposed parallel to the longitudinal axis of the cylindrical body of the retrieval device. For example, as shown in FIG. 2B, each of antennas 28a and 28b is longitudinally aligned with at least one of the fifth and sixth struts of the cell structures residing in the central body portion 25 of the retrieval device 20. An advantage of such a configuration is that it reduces the risk of the retrieval device buckling when being pushed by the elongate wire 16.

Figure 4:
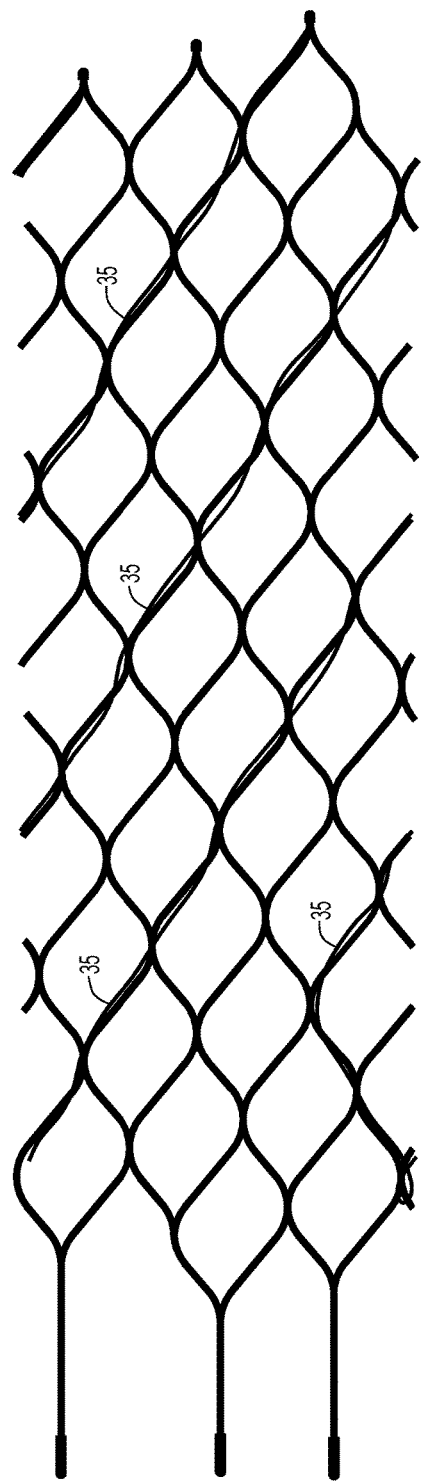
FIG. 4 illustrates the obstruction retrieval device of FIG. 2B with a radiopaque element dispersed therein.
Figure 5:
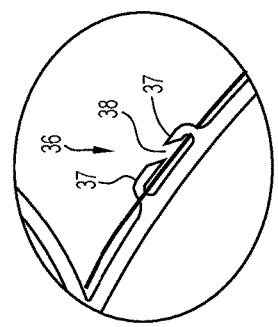
FIG. 5 is a perspective view of a strut of an obstruction retrieval device having a feature for receiving therein a portion of a radiopaque element.

It is sometimes important for the treating clinician to visualize the retrieval device during an obstruction remove procedure to ensure that the device is properly placed before being deployed. For this reason, according to some implementations the retrieval device 20 is equipped with a radiopaque wire or ribbon 35 that meanders between the inside and outside of the cylindrical body 21 in a pattern that preferably extends along a substantial portion of the length of the cylindrical body as shown in FIG. 4. According to some implementations at least some of the struts of the retrieval device comprise a retaining feature 36, as shown in FIG. 5, through which the radiopaque wire or ribbon 35 passes as it meanders through the cylindrical body 21 of the retrieval device 20. According to some implementations the retaining features 36 are formed during a laser cutting operation employed to construct the struts of the retrieval device. As discussed above, according to some implementations the retrieval device is constructed by laser cutting a cylindrical metallic tube to form the struts of the device. In the implementation of FIG. 5 the retaining feature 36 includes two L-shape like members 37 that are separated by a gap 38 through which the radiopaque wire or ribbon 35 passes when it assembled on the strut.

According to some implementations, the radiopaque wire or ribbon 35 is assembled on the retrieval device when the retrieval device is in a fully expanded state, and as such, does not impact the outward radial force of the retrieval device during its use. Further, according to other implementations, the radiopaque wire or ribbon 35 is assembled on the retrieval device in a manner such that it does not affect the flexure stiffness of the retrieval device.

While the foregoing disclosure contains many specifics, these should not be construed as limitations on the scope of what is claimed or of what may be claimed, but rather as descriptions of features specific to particular exemplary implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Variations, modifications and enhancements to the described examples and implementations and other implementations may be made based on what is disclosed.

The following clauses disclose in an unlimited way additional implementations, with each clause representing an implementation. Additional implementations are represented by one or more of the implementations of one group or groups of clauses with one or more implementations of another group or groups of clauses. Group A through C clauses are provided.

Group A clauses:

Clause 1. A device for capturing and removing an obstruction in a bodily duct of a patient, the device comprising:

a cylindrical body having a circumference and a longitudinal axis and including a plurality of closed cell structures arranged in a plurality of diagonal rows disposed around the longitudinal axis, at least some of the plurality of closed cell structures being substantially the same shape and size, at least some of the closed cells structures of substantially same shape and size occupying a same circumferential location in the cylindrical body and being longitudinally separated from one another by no less than two diagonal rows of closed cell structures.

Clause 2. The device according to clause 1, wherein the plurality of closed cell structures occupying a same circumferential location are longitudinally separated by no less than three diagonal rows of closed cell structures.

Clause 3. The device according to clause 1, wherein the plurality of closed cell structures occupying a same circumferential location and are longitudinally separated by no less than four diagonal rows closed cell structures.

Clause 4. The device according to clause 1, wherein the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut.

Clause 5. The device according to clause 4, wherein the proximal and distal ends of the fifth strut are longitudinally aligned with one another and residing at a first circumferential location, the proximal and distal ends of the sixth strut being longitudinally aligned with one another and residing at a second circumferential location, the second circumferential location being spaced apart from the first circumferential location.

Clause 6. The device according to clause 5, wherein when the device is cut longitudinally and laid flat on a surface at least one of the fifth and sixth struts is straight.

Clause 7. The device according to clause 5, wherein when the device is cut longitudinally and laid flat on a surface each of the fifth and sixth struts is straight.

Clause 8. The device according to clause 5, wherein the proximal end of the first strut being coupled to the proximal end of the second strut at a first longitudinal location, the distal end of the third strut being coupled to the distal end of the fourth strut at a second longitudinal location distal to the first longitudinal location, the distal end of the first strut being coupled to the proximal end of the fifth strut at a third longitudinal location, the proximal end of the third strut being coupled to the distal end of the fifth strut at a fourth longitudinal location, the distal end of the second strut being coupled to the proximal end of the sixth strut at a fifth longitudinal location, the proximal end of the fourth strut being coupled to the distal end of the sixth strut at a sixth longitudinal location.

Clause 9. The device according to clause 8, wherein the fourth longitudinal location and fifth longitudinal location are circumferentially aligned.

Clause 10. The device according to clause 5, further comprising a first antenna having a proximal end and a distal end, the cylindrical body coupled to the distal end of the first antenna, when the device is cut longitudinally and laid flat on a surface at least a portion of the first antenna is straight, the at least portion being longitudinally aligned with the proximal and distal ends of at least one of the fifth struts and/or with the proximal and distal ends of at least one of the sixth struts.

Clause 11. The device according to clause 7, further comprising a first antenna having a proximal end and a distal end, the cylindrical body coupled to the distal end of the first antenna, wherein when the device is cut longitudinally and laid flat on a surface at least a portion of the first antenna is straight, the at least portion being longitudinally aligned with at least one of the fifth struts and/or at least one of the sixth struts.

Clause 12. The device according to clause 10, further comprising a second antenna having a proximal end and a distal end, wherein when the device is cut longitudinally and laid flat on a surface at least a portion of the second antenna is straight, the at least portion of the second antenna being longitudinally aligned with the proximal and distal ends of at least one of the fifth struts and/or with the proximal and distal ends of at least one of the sixth struts.

Clause 13. The device according to clause 10, further comprising a second antenna having a proximal end and a distal end, wherein when the device is cut longitudinally and laid flat on a surface at least a portion of the second antenna is straight, the at least portion being longitudinally aligned with at least one of the fifth struts or at least one of the sixth struts.

Clause 14. The device according to clause 1, wherein the cylindrical body has an open distal end.

Clause 15. The device according to clause 10, further comprising an elongate wire having a proximal end and a distal end, the proximal end of the first antenna being coupled to the distal end of the elongate wire.

Clause 16. The device according to clause 11, further comprising an elongate wire having a proximal end and a distal end, the proximal end of the first antenna being coupled to the distal end of the elongate wire.

Clause 17. The device according to clause 5, wherein when the device is cut longitudinally and laid flat on a surface at least a portion of each of the first, second, third and fourth struts is curved.

Clause 18. The device according to clause 17, wherein when the device is cut longitudinally and laid flat on a surface at least a portion of each of the first, second, third and fourth struts is straight.

Clause 19. The device according to clause 5, wherein each of the first, second, third and fourth struts has a proximal end portion, a distal end portion and a mid-portion, the mid-portion located between the proximal and distal end portions, the first and second end portions being curved and the mid-portion being straight when the device is cut longitudinally and laid flat on a surface.

Clause 20. The device according to clause 4, wherein among the plurality of cell structures, adjacent cell structures share at least one of the first, second, third, fourth, fifth or sixth struts with one another, the adjacent cell structures being both longitudinally and circumferentially offset from one another.

Clause 21. The device according to clause 10, further comprising a second antenna and a third antennal, each of the second and third antennas having a proximal end and a distal end, each of the distal ends of the first, second and third antennas being coupled to the cylindrical body at different circumferential locations from one another.

Clause 22. The device according to clause 21, further comprising an elongate wire coupled to the proximal end of each of the first, second and third antennas.

Clause 23. The device according to clause 8, wherein the first longitudinal location and the second longitudinal location are not longitudinally aligned with one another.

Clause 24. The device according to clause 23, wherein each of the first, second, third and fourth struts has a proximal end portion, a distal end portion and a mid-portion, the mid-portion located between the proximal and distal end portions, the first and second end portions being curved and the mid-portion being straight when the device is cut longitudinally and laid flat on a surface, the first longitudinal location and the second longitudinal location are not longitudinally aligned with one another.

Clause 25. The device according to clause 19, wherein the mid-portion of one or more or all of the first, second, third and fourth struts occupies 20% to 80% of an overall length of the respective strut.

Clause 26. The device according to clause 19, wherein the mid-portion of one or more or all of the first, second, third and fourth struts occupies 30% to 70% of an overall length of the respective strut.

Group B clauses:

Clause 1. A device for capturing an obstruction in a bodily duct of a patient, the device comprising:

a cylindrical body having a circumference and a longitudinal axis and including a plurality of cell structures of the same size and shape arranged in diagonal rows around the longitudinal axis, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight.

Clause 2. The device according to clause 1, wherein each of the first, second, third and fourth struts has a proximal end portion, a distal end portion and a mid-portion, the mid-portion being located between the proximal and distal end portions, the first and second end portions being curved and the mid-portion being straight when the device is cut longitudinally and laid flat on a surface.

Clause 3. The device according to clause 1, wherein when the device is cut longitudinally and laid flat on a surface at least one of the fifth and sixth struts is straight.

Clause 4. The device according to clause 1, wherein when the device is cut longitudinally and laid flat on a surface each of the fifth and sixth struts is straight.

Clause 5. The device according to clause 2, wherein when the device is cut longitudinally and laid flat on a surface at least one of the fifth and sixth struts is straight.

Clause 6. The device according to clause 2, wherein when the device is cut longitudinally and laid flat on a surface each of the fifth and sixth struts is straight.

Clause 7. The device according to clause 1, wherein a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least two intervening cell structures.

Clause 8. The device according to clause 1, wherein a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least three intervening cell structures.

Clause 9. The device according to clause 1, wherein a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least two intervening cell structures.

Clause 10. The device according to clause 1, wherein a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least three intervening cell structures.

Clause 11. The device according to clause 1, wherein a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least four intervening cell structures.

Clause 12. The device according to clause 1, wherein at least some of the plurality of cell structures occupy a same circumferential location and are longitudinally separated by no less than two diagonal rows.

Clause 13. The device according to clause 1, wherein at least some of the plurality of cell structures occupy a same circumferential location and are longitudinally separated by no less than three diagonal rows.

Clause 14. The device according to clause 1, wherein at least some of the plurality of cell structures occupy a same circumferential location and are longitudinally separated by no less than four diagonal rows.

Clause 15. The device according to clause 1, wherein the distal end of the fifth strut and the proximal end of the sixth strut are circumferentially aligned.

Clause 16. The device according to clause 1, wherein the proximal end of the first strut is coupled to the proximal end of the second strut at a first longitudinal location, the distal end of the third strut being coupled to the distal end of the fourth strut at a second longitudinal location distal to the first longitudinal location, the distal end of the first strut being coupled to the proximal end of the fifth strut at a third longitudinal location, the proximal end of the third strut being coupled to the distal end of the fifth strut at a fourth longitudinal location, the distal end of the second strut being coupled to the proximal end of the sixth strut at a fifth longitudinal location, the proximal end of the fourth strut being coupled to the distal end of the sixth strut at a sixth longitudinal location.

Clause 17. The device according to clause 16, wherein the fourth longitudinal location and fifth longitudinal location are circumferentially aligned.

Clause 18. The device according to clause 16, wherein the first longitudinal location and second longitudinal location are not longitudinally aligned.

Clause 19. The device according to clause 1, further comprising a first antenna having a proximal end and a distal end, the cylindrical body coupled to the distal end of the first antenna, when the device is cut longitudinally and laid flat on a surface at least a portion of the first antenna is straight, the at least portion being longitudinally aligned with the proximal and distal ends of at least one of the fifth struts and/or with the proximal and distal ends of at least one of the sixth struts.

Clause 20. The device according to clause 19, wherein when the device is cut longitudinally and laid flat on a surface at least one of the fifth and sixth struts is straight.

Clause 21. The device according to clause 19, wherein when the device is cut longitudinally and laid flat on a surface each of the fifth and sixth struts is straight.

Clause 22. The device according to clause 19, further comprising a second antenna having a proximal end and a distal end, wherein when the device is cut longitudinally and laid flat on a surface at least a portion of the second antenna is straight, the at least portion of the second antenna being longitudinally aligned with the proximal and distal ends of at least one of the fifth struts and/or with the proximal and distal ends of at least one of the sixth struts.

Clause 23. The device according to clause 1, wherein the cylindrical body has an open distal end.

Clause 24. The device according to clause 19, further comprising an elongate wire having a proximal end and a distal end, the proximal end of the first antenna being coupled to the distal end of the elongate wire.

Clause 25. The device according to clause 22, further comprising an elongate wire having a proximal end and a distal end, the proximal end of each of the first antenna and second antenna being coupled to the distal end of the elongate wire.

Clause 26. The device according to clause 1, wherein among the plurality of cell structures, adjacent cell structures share at least one of the first, second, third, fourth, fifth or sixth struts with one another, the adjacent cell structures being both longitudinally and circumferentially offset from one another.

Clause 27. The device according to clause 19, further comprising a second antenna and a third antennal, each of the second and third antennas having a proximal end and a distal end, each of the distal ends of the first, second and third antennas being coupled to the cylindrical body at different circumferential locations from one another.

Clause 28. The device according to clause 27, further comprising an elongate wire coupled to the proximal end of each of the first, second and third antennas.

Clause 29. The device according to clause 1, wherein the first portion of one or more or all of the first, second, third and fourth struts occupies 20% to 80% of an overall length of the respective strut.

Clause 30. The device according to clause 1, wherein the first portion of one or more or all of the first, second, third and fourth struts occupies 30% to 70% of an overall length of the respective strut.

Clause 31. The device according to clause 2, wherein the mid-portion of one or more or all of the first, second, third and fourth struts occupies 20% to 80% of an overall length of the respective strut.

Clause 32. The device according to clause 2, wherein the mid-portion of one or more or all of the first, second, third and fourth struts occupies 30% to 70% of an overall length of the respective strut.

Group C clauses:

Clause 1. A device for capturing an obstruction in a bodily duct of a patient, the device comprising:

a cylindrical body having a circumference and a longitudinal axis and including a plurality of cell structures arranged around the longitudinal axis, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut at a first longitudinal location, the distal end of the third strut being coupled to the distal end of the fourth strut at a second longitudinal location distal to the first longitudinal location, the distal end of the first strut being coupled to the proximal end of the fifth strut at a third longitudinal location, the proximal end of the third strut being coupled to the distal end of the fifth strut at a fourth longitudinal location, the distal end of the second strut being coupled to the proximal end of the sixth strut at a fifth longitudinal location, the proximal end of the fourth strut being coupled to the distal end of the sixth strut at a sixth longitudinal location, each of the third and fourth longitudinal locations being longitudinally aligned with one another and residing at a first circumferential location, each of the fifth and sixth longitudinal locations being longitudinally aligned with one another and residing at a second circumferential location, the second circumferential location being spaced apart from the first circumferential location.

Clause 2. The device according to clause 1, wherein when the device is cut longitudinally and laid flat on a surface at least one of the fifth and sixth struts is straight and arranged parallel to the longitudinal axis.

Clause 3. The device according to clause 1, wherein when the device is cut longitudinally and laid flat on a surface each of the fifth and sixth struts is straight and arranged parallel to the longitudinal axis.

Clause 4. The device according to clause 1, wherein the fourth longitudinal location and fifth longitudinal location are circumferentially aligned.

Clause 5. The device according to clause 1, further comprising a first antenna having a proximal end and a distal end, the cylindrical body coupled to the distal end of the first antenna, wherein when the device is cut longitudinally and laid flat on a surface at least a portion of the first antenna is straight, at least a portion of the first antenna is straight and longitudinally aligned with the proximal and distal ends of at least one of the fifth struts and/or with the proximal and distal ends of at least one of the sixth struts.

Clause 6. The device according to clause 2, further comprising a first antenna having a proximal end and a distal end, the cylindrical body coupled to the distal end of the first antenna, wherein when the device is cut longitudinally and laid flat on a surface at least a portion of the first antenna is straight, the at least portion being longitudinally aligned with at least one of the fifth struts and/or at least one of the sixth struts.

Clause 7. The device according to clause 3, wherein when the device is cut longitudinally and laid flat on a surface at least a portion of the first antenna is straight, the at least portion being longitudinally aligned with at least one of the fifth struts and/or at least one of the sixth struts.

Clause 8. The device according to clause 5, further comprising a second antenna having a proximal end and a distal end, wherein when the device is cut longitudinally and laid flat on a surface at least a portion of the second antenna is straight, the at least portion of the second antenna being longitudinally aligned with the proximal and distal ends of at least one of the fifth struts and/or with the proximal and distal ends of at least one of the sixth struts.

Clause 9. The device according to clause 7, further comprising a second antenna having a proximal end and a distal end, wherein when the device is cut longitudinally and laid flat on a surface at least a portion of the second antenna is straight, the at least portion being longitudinally aligned with at least one of the fifth struts or at least one of the sixth struts.

Clause 10. The device according to clause 1, wherein the cylindrical body has an open distal end.

Clause 11. The device according to clause 5, further comprising an elongate wire having a proximal end and a distal end, the proximal end of the first antenna being coupled to the distal end of the elongate wire.

Clause 12. The device according to clause 5, further comprising an elongate wire having a proximal end and a distal end, the proximal end of the first antenna being coupled to the distal end of the elongate wire.

Clause 13. The device according to clause 8, further comprising an elongate wire having a proximal end and a distal end, the proximal end of each of the first antenna and second antenna being coupled to the distal end of the elongate wire.

Clause 14. The device according to clause 1, wherein when the device is cut longitudinally and laid flat on a surface at least a portion of each of the first, second, third and fourth struts is curved.

Clause 15. The device according to clause 14, wherein when the device is cut longitudinally and laid flat on a surface at least a portion of each of the first, second, third and fourth struts is straight.

Clause 16. The device according to clause 1, wherein each of the first, second, third and fourth struts has a proximal end portion, a distal end portion and a mid-portion, the mid-portion located between the proximal and distal end portions, the first and second end portions being curved and the mid-portion being straight when the device is cut longitudinally and laid flat on a surface.

Clause 17. The device according to clause 1, wherein among the plurality of cell structures, adjacent cell structures share at least one of the first, second, third, fourth, fifth or sixth struts with one another, the adjacent cell structures being both longitudinally and circumferentially offset from one another.

Clause 18. The device according to clause 5, further comprising a second antenna and a third antennal, each of the second and third antennas having a proximal end and a distal end, each of the distal ends of the first, second and third antennas being coupled to the cylindrical body at different circumferential locations from one another.

Clause 19. The device according to clause 20, further comprising an elongate wire coupled to the proximal end of each of the first, second and third antennas.

Clause 20. The device of clause 1, wherein the first longitudinal location and the second longitudinal location are not longitudinally aligned with one another.

Clause 21. The device of claim 16, wherein the first longitudinal location and the second longitudinal location are not longitudinally aligned with one another.

Clause 22. The device according to clause 15, wherein the straight portion of one or more or all of the first, second, third and fourth struts occupies 20% to 80% of an overall length of the respective strut.

Clause 23. The device according to clause 15, wherein the first portion of one or more or all of the first, second, third and fourth struts occupies 30% to 70% of an overall length of the respective strut.

Clause 31. The device according to clause 16, wherein the mid-portion of one or more or all of the first, second, third and fourth struts occupies 20% to 80% of an overall length of the respective strut.

Clause 32. The device according to clause 16, wherein the mid-portion of one or more or all of the first, second, third and fourth struts occupies 30% to 70% of an overall length of the respective strut.

What is claimed is:

1. A device for capturing an obstruction in a bodily duct of a patient, the device comprising:
   a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end,
   the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, the cylindrical body having a proximal end and a distal end and a first of the plurality of cell structures is longitudinally aligned with a second of the plurality of cell structures, the first of the plurality of cell structures being located in the cylindrical body proximally to the second of the plurality of cell structures, each of the first and second plurality of cell structures having a proximal end and a distal end, an imaginary longitudinal straight line running parallel to the longitudinal axis and joining the distal end of the first of the plurality of cell structures with the proximal end of the second of the plurality of cell structures intersects at least two intervening cell structures, the second of the plurality of cell structures being located nearer the first of the plurality of cell structures than any of another of the plurality of cell structures that are longitudinally aligned with the first of the plurality of cell structures.

2. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least three intervening cell structures, the second of the plurality of cell structures being located nearer the first of the plurality of cell structures than any of another of the plurality of cell structures that are longitudinally aligned with the first of the plurality of cell structures.

3. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, a first of the plurality of cell structures is longitudinally aligned with a second of the plurality of cell structures, an imaginary longitudinal straight line running parallel to the longitudinal axis and joining the fifth struts or the sixth struts of the first and second cell structures intersects at least four intervening cell structures, the second of the plurality of cell structures being located nearer the first of the plurality of cell structures than any of another of the plurality of cell structures that are longitudinally aligned with the first of the plurality of cell structures.

4. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, a first of the plurality of cell structures and a second of the plurality of cell structures occupy a same circumferential location and are longitudinally separated by no less than two diagonal rows, the second of the plurality of cell structures being located nearer the first of the plurality of cell structures than any of another of the plurality of cell structures that are longitudinally aligned with the first of the plurality of cell structures.

5. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, a first of the plurality of cell structures and a second of the plurality of cell structures occupy a same circumferential location and are longitudinally separated by no less than three diagonal rows, the second of the plurality of cell structures being located nearer the first of the plurality of cell structures than any of another of the plurality of cell structures that are longitudinally aligned with the first of the plurality of cell structures.

6. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, a first of the plurality of cell structures and a second of the plurality of cell structures occupy a same circumferential location and are longitudinally separated by no less than four diagonal rows, the second of the plurality of cell structures being located nearer the first of the plurality of cell structures than any of another of the plurality of cell structures that are longitudinally aligned with the first of the plurality of cell structures.

7. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, the distal end of the fifth strut and the proximal end of the sixth strut are circumferentially aligned.

8. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being coupled to the proximal end of the second strut, the distal end of the third strut being coupled to the distal end of the fourth strut, the distal end of the first strut being coupled to the proximal end of the fifth strut, the proximal end of the third strut being coupled to the distal end of the fifth strut, the distal end of the second strut being coupled to the proximal end of the sixth strut, the proximal end of the fourth strut being coupled to the distal end of the sixth strut, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, when the device is cut longitudinally and laid flat on a surface at least a first portion of each of the first, second, third and fourth struts is curved and at least a second portion of each of the first, second, third and fourth struts is straight, the device further comprising a first antenna having a proximal end and a distal end, the cylindrical body coupled to the distal end of the first antenna, when the device is cut longitudinally and laid flat on a surface at least a portion of the first antenna is straight, the at least a portion of the first antenna being longitudinally aligned with the proximal and distal ends of at least one of the fifth struts and/or with the proximal and distal ends of at least one of the sixth struts.

9. The device according to claim 8, wherein when the device is cut longitudinally and laid flat on a surface at least one of the fifth and sixth struts is straight.

10. The device according to claim 8, wherein when the device is cut longitudinally and laid flat on a surface each of the fifth and sixth struts is straight.

11. The device according to claim 8, further comprising a second antenna having a proximal end and a distal end, wherein when the device is cut longitudinally and laid flat on a surface at least a portion of the second antenna is straight, the at least a portion of the second antenna being longitudinally aligned with the proximal and distal ends of at least one of the fifth struts and/or with the proximal and distal ends of at least one of the sixth struts.

12. The device according to claim 8, further comprising an elongate wire having a proximal end and a distal end, the proximal end of the first antenna being coupled to the distal end of the elongate wire.

13. The device according to claim 11, further comprising an elongate wire having a proximal end and a distal end, the proximal end of each of the first antenna and second antenna being coupled to the distal end of the elongate wire.

14. The device according to claim 8, further comprising a second antenna and a third antenna, each of the second and third antennas having a proximal end and a distal end, each of the distal ends of the first, second and third antennas being coupled to the cylindrical body at different circumferential locations from one another.

15. The device according to claim 14, further comprising an elongate wire coupled to the proximal end of each of the first, second and third antennas.

16. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being directly coupled to the proximal end of the second strut at a first longitudinal location, the distal end of the third strut being directly coupled to the distal end of the fourth strut at a second longitudinal location distal to the first longitudinal location, the distal end of the first strut being directly coupled to the proximal end of the fifth strut at a third longitudinal location, the proximal end of the third strut being directly coupled to the distal end of the fifth strut at a fourth longitudinal location, the distal end of the second strut being directly coupled to the proximal end of the sixth strut at a fifth longitudinal location, the proximal end of the fourth strut being directly coupled to the distal end of the sixth strut at a sixth longitudinal location, the fourth longitudinal location being proximal to the sixth longitudinal location, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, the fourth longitudinal location and fifth longitudinal location being circumferentially aligned, when the device is cut longitudinally and laid flat on a surface at least a first portion of each of the first, second, third and fourth struts is curved and at least a second portion of each of the first, second, third and fourth struts is straight.

17. A device for capturing an obstruction in a bodily duct of a patient, the device comprising:

a cylindrical body having a circumference and a longitudinal axis and including a plurality of cell structures formed by struts, the plurality of cell structures being of the same size and shape and arranged in diagonal rows around the longitudinal axis, the plurality of cell structures including first, second, third, fourth and fifth cell structures, the first cell structure being surrounded by the second, third, fourth and fifth cell structures and sharing at least one strut with each of the second, third, fourth and fifth cell structures, the plurality of cell structures each includes first, second, third, fourth, fifth and sixth struts, each of the first, second, third, fourth, fifth and sixth struts having a proximal end and a distal end, the proximal end of the first strut being directly coupled to the proximal end of the second strut at a first longitudinal location, the distal end of the third strut being directly coupled to the distal end of the fourth strut at a second longitudinal location distal to the first longitudinal location, the distal end of the first strut being directly coupled to the proximal end of the fifth strut at a third longitudinal location, the proximal end of the third strut being directly coupled to the distal end of the fifth strut at a fourth longitudinal location, the distal end of the second strut being directly coupled to the proximal end of the sixth strut at a fifth longitudinal location, the proximal end of the fourth strut being directly coupled to the distal end of the sixth strut at a sixth longitudinal location, the fourth longitudinal location being proximal to the sixth longitudinal location, the proximal and distal ends of the fifth strut being longitudinally aligned with one another and residing at a first circumferential location, the proximal and distal ends of the sixth strut being longitudinally aligned with one another and residing at a second circumferential location, the second circumferential location being spaced apart from the first circumferential location, the first longitudinal location and second longitudinal location are not longitudinally aligned, when the device is cut longitudinally and laid flat on a surface at least a first portion of each of the first, second, third and fourth struts is curved and at least a second portion of each of the first, second, third and fourth struts is straight.

* * * * *